(12) United States Patent
Sardo

(10) Patent No.: US 9,706,772 B2
(45) Date of Patent: Jul. 18, 2017

(54) METHOD FOR FUNGICIDAL AND/OR BACTERICIDAL TREATMENT OF RESISTANT STRAINS USING ESSENTIAL OIL(S)

(75) Inventor: Alberto Sardo, Chateaurenaud (FR)

(73) Assignee: XEDA INTERNATIONAL, Saint Andiol (FR)

( * ) Notice: Subject to any disclaimer, the term of this patent is extended or adjusted under 35 U.S.C. 154(b) by 0 days.

(21) Appl. No.: 13/823,768

(22) PCT Filed: Oct. 4, 2011

(86) PCT No.: PCT/FR2011/052315
§ 371 (c)(1),
(2), (4) Date: Mar. 15, 2013

(87) PCT Pub. No.: WO2013/050662
PCT Pub. Date: Apr. 11, 2013

(65) Prior Publication Data
US 2013/0178489 A1    Jul. 11, 2013

(51) Int. Cl.
| | |
|---|---|
| *A61K 31/4164* | (2006.01) |
| *A61K 31/4168* | (2006.01) |
| *A01N 31/16* | (2006.01) |
| *A01N 25/00* | (2006.01) |
| *A01N 31/08* | (2006.01) |
| *A01N 65/00* | (2009.01) |
| *A01N 65/24* | (2009.01) |
| *A01N 65/28* | (2009.01) |
| *A23L 3/3472* | (2006.01) |
| *A23L 3/349* | (2006.01) |
| *A23L 3/3499* | (2006.01) |
| *A23L 3/3526* | (2006.01) |
| *A23L 3/3544* | (2006.01) |
| *A01N 43/54* | (2006.01) |

(52) U.S. Cl.
CPC ............ *A01N 31/16* (2013.01); *A01N 25/00* (2013.01); *A01N 31/08* (2013.01); *A01N 43/54* (2013.01); *A01N 65/00* (2013.01); *A01N 65/24* (2013.01); *A01N 65/28* (2013.01); *A23L 3/349* (2013.01); *A23L 3/3472* (2013.01); *A23L 3/3499* (2013.01); *A23L 3/3526* (2013.01); *A23L 3/3544* (2013.01)

(58) Field of Classification Search
CPC . A61K 31/05; A61K 31/4164; A61K 31/4168
USPC .......................................................... 514/295
See application file for complete search history.

(56) References Cited

U.S. PATENT DOCUMENTS

2006/0228458 A1* 10/2006 Sardo ............................ 426/601
2008/0175926 A1    7/2008 Bompeix et al.

FOREIGN PATENT DOCUMENTS

| CN | 101507433 | 8/2009 |
| EP | 1 854 353 A1 | 11/2007 |

OTHER PUBLICATIONS

International Search Report, dated Aug. 21, 2012, from corresponding PCT application.
J.H. Kim et al., "Use of chemosensitization to overcome fludioxonil resistance in Penicillium expansum", Letters in Applied Microbiology, 2010, pp. 177-183.
Kavitha Palaniappan et al., "Use of natural antimicrobials to increase antibiotic susceptibility of drug resistant bacteria", International Journal of Food Mictrobiology, 2010, pp. 164-168, vol. 140, No. 2-3, XP-002624024.
Jong H. Kim et al., "Augmenting the activity of antifungal agents against aspergilli using structural analogues of benzoic acid as chemosensitizing agents", Fungal Biology, 2010, pp. 817-824, vol. 114, No. 10.
Jong H. Kim et al., "Chemosensitization of fungal pathogens to antimicrobial agents using benzo analogs", FEMS Microbiology Letters, 2008, pp. 64-72, vol. 281, No. 1.
N.C.G. Faria et al., "Enhanced activity of antifungal drugs using natural phenolics against yeast strains of Candida and Cryptococcus", Letters in Applied Microbiology, 2011, pp. 506-513, vol. 52, No. 5.
R. Montes-Belmont et al., "Control of Aspergillus flavus in Maize with Plant Essential Oils and Their Components", Journal of Food Protection, 1998, pp. 616-619, vol. 61, No. 5, XP-000886016.
He Yan-Bioa, et al. "Inhibition Effects of *Syzygium aromaticum* (L.) Extracts against Colletotrichum gloeosporioides and *Fusarium oxysporum* f. sp. cubense," Jountal of Sichuan Agricultural University, vol. 24, No. 4, Dec. 2006, pp. 394-397, 404.
Tingyu He et al. (2008).

* cited by examiner

*Primary Examiner* — Yong Chong
(74) *Attorney, Agent, or Firm* — Young & Thompson

(57) ABSTRACT

The present invention relates to a method for fungicidal and/or bactericidal treatment of plants or foodstuffs using one or more essential oil(s) that enable the treatment of strains resistant to synthetic fungicides and/or bactericides.

9 Claims, 2 Drawing Sheets

METHOD FOR FUNGICIDAL AND/OR BACTERICIDAL TREATMENT OF RESISTANT STRAINS USING ESSENTIAL OIL(S)

The present invention relates to a method for treating plants or foodstuffs, in particular fruits and/or vegetables. In fact, it is important that plants have the ability to resist the attacks of fungi and bacteria that reduce the quantity and quality of plants or foodstuffs produced and which, in extreme cases, can also lead to the death of the infected plants. It is also important that the fruits and vegetables retain their taste and maintain an appealing appearance when they are placed on the market so as to ensure their rapid consumption. However, after they are harvested, the fruits and vegetables are frequently stored for relatively long periods of time before they are put on the market. The phenomena that are likely to alter the appearance and the taste of the fruits and vegetables are mainly the proliferation of fungi and bacteria on their surfaces before and/or after harvesting. Such deterioration and damage caused set in even faster when micro-cuts and scrapes appear on the skin when the fruits and vegetables are stored or being handled.

In order to prevent such deterioration and damage, the fruits and/or vegetables are generally treated with fungicides and/or bactericides.

However, fungi and bacteria develop resistances to synthetic fungicides and/or bactericides that are commonly used.

Thus, it is known that several types of fungi such as penicillium have developed resistance, with respect to benzimidazoles for example.

The resistance to fungicides/bactericides develops when some strains are naturally resistant or become resistant, for example by mutation of their DNA, and later are selected by applying fungicides/bactericides. Therefore the population gets further enriched as these resistant strains gradually develop.

Therefore there is a need to find alternative treatment means for these resistant strains of fungi and/or bacteria.

The fungicidal and/or bactericidal activity of essential oils is already known. Thus, the patent application FR9815305 describes the fungicidal and bactericidal activity of various terpenes contained in the essential oils.

Surprisingly, it was found that essential oils have a specific activity against the strains of fungi and/or bacteria that are resistant to synthetic fungicides and/or bactericides.

The invention therefore relates to a method for fungicidal and/or bactericidal treatment of one or more phytopathogenic strain(s) of fungi and/or bacteria resistant to one or more synthetic fungicidal and/or bactericidal agent(s) that comprising the application of a composition comprising one or more essential oil(s) and/or terpene active ingredient(s) contained therein on plants or foodstuffs that are infected by a said strain.

The plants or foodstuffs in particular refer to small plants and to their harvests, and in particular to fruits and vegetables, before and after harvesting.

The term "essential oil" refers to any product, generally fragrant and having a complex composition, obtained from plant—vegetable raw materials, in particular either through steam distillation, dry distillation or through an appropriate mechanical process without heating.

The essential oils are most often separated from the aqueous phase through a physical process not leading to a significant change in their composition. Their preparation is carried out according to methods known to the person skilled in the art.

With regard to essential oils, one could in particular mention clove oil, cinnamon oil, thyme oil, oregano oil or peppermint oil; with respect to terpene active ingredients contained in the said essential oils, one could mention eugenol, iso-eugenol, cinnamaldehyde, thymol, carvacrol and carvone.

According to one particular aspect, the said composition comprises a mixture of thymol, carvacrol and eugenol.

It is understood that the said terpene active ingredients can be isolated from the essential oils or prepared synthetically or semi-synthetically.

The term "resistant strains" refers to strains of fungi and/or bacteria that have little or no sensitivity to a fungicidal and/or bactericidal agent; for example, strains for which the application of fungicides and/or bactericides destroys only 60% or less of said strains. This resistance can be naturally occurring or result from a genetic mutation.

With regard to synthetic fungicides and/or bactericides, these refer to agents that are not derived from natural products such as plants; this expression thus excludes the terpene active ingredients that are contained in the said essential oils. With respect to synthetic fungicides and/or bactericides that may create resistance, the following may be cited:

By way of fungicides, benzimidazoles such as thiabendazole, or their precursors such as thiophanates; anillopyrimidines such as pyrimethanil; imidazoles such as imazalil; phenylamines such as metalaxyl; nitrogen heterocycles such as fludioxonil.

By way of fungicides/bactericides, phenol; quaternary ammonium such as alkyl dimethyl benzyl ammonium chloride or peracetic acid.

As an example of phytopathogenic fungi with resistance to one or more synthetic fungicidal and/or bactericidal agents, one could in particular list the genera *Penicillium, Botrytis, Monilinia, Gloeosporium, Phytophtora, Fusarium, Alternaria, Geotrichum, Venturia, Rhizopus, Phoma, Helminthosporium*; and more particularly the species *Penicillium* spp, among which *Penicillium digitatum, Penicillium expansum,* or *Penicillium italicum; Botrytis* spp. among which *Botrytis cinerea, Monilinia* spp. among which *Monilinia fructicola, Monilinia fructigena* or *Monilinia laxa; Gloeosporium* spp. among which *Gloeosporium album, Gloeosporium fructigenum* or *Gloeosporium perennans; Phytophtora* spp; *Fusarium* spp. or even *Alternaria alternata; Geotrichum candidum; Venturia inequalis; Rhizopus nigricans; Phoma exigua* or *Helminthosporium Rhizoctonia solani*.

As an example of phytopathogenic bacteria with resistance to one or more synthetic fungicidal and/or bactericidal agents, one could in particular cite *Pseudomonas syringae, Escherichia coli, Erwinia amylovora* or *Erwinia carotovora*.

More particularly, *Penicillium* spp. has strains resistant to imazalil; *Penicillium digitatum* and *Penicillium expansum* have strains resistant to pyrimethanil; *Pseudomonas syringae* has strains resistant to quaternary ammonium; *Botrytis cinerea* has strains resistant to benzimidazoles; *Monilinia fructicola* has strains resistant to pyrimethanil.

Without being bound by a theory, it has been unexpectedly discovered that essential oils that may have a modest fungicidal and/or bactericidal activity on sensitive strains become very active against resistant strains. Essential oils probably have a multi-site activity and as a result they do not lead to the creation of resistant strains. As a result, their combinations with synthetic agents make it possible to thereby avoid genetic selection leading to the development of resistant strains.

In an advantageous manner, the essential oil(s) and/or the terpene active ingredient(s) that they contain may be used in combination with one or more fungicidal and/or bactericidal agent(s). Not only does this combination make it possible to treat both the resistant strains as well as the sensitive strains, but it has also unexpectedly been discovered that the activity on the resistant strains was thereby enhanced by using this combination.

Preferably, the essential oil(s) and the fungicidal and/or bactericidal agent(s) are applied in a ratio (essential oil(s) part/fungicidal and/or bactericidal agent(s) part) comprised between 0.3 and 3.

Generally, the said fungicidal and/or bactericidal agent(s) is (are) that (those) to which the strain is resistant, such as the ones previously mentioned.

Among examples of the preferred combination are, the following are in particular included:
 imazalil and thymol and/or thyme oil,
 carvacrol and/or oregano oil and thiabendazole,
 pyrimethanil and eugenol/or cloves oil,
 alkyl dimethyl benzyl ammonium chloride and cinnamon oil.

According to a preferred embodiment, the fungicidal and/or bactericidal agent(s) is (are) applied simultaneously with the essential oil(s) and/or the terpene active ingredient(s) contained therein, such as for example within a same composition or separately by means of distinct compositions.

Application of the compositions according to the invention may be carried out before or after harvesting.

Generally, the compositions according to the invention are in the form of an emulsifiable concentrate which can be dispersed in water before they are applied. More particularly, the emulsifiable concentrate includes in particular one or more essential oil(s) and/or the terpene active ingredient(s) contained therein with lecithin and/or derivatives. The emulsifiable concentrate may, in addition, comprise one or more emulsifiers. Generally, the emulsifiable concentrate may consist of in particular one or more essential oil(s) and/or the terpene active ingredient(s) contained therein, lecithin and/or derivatives and possibly one or more emulsifiers.

According to the invention, the term "lecithins and/or derivatives" refers to one or more compounds selected from among derivatives of phosphatidylcholine and/or its derivatives, such as phosphatidylcholine, phosphatidylinositol, phosphatidyl-ethanolamine and/or phosphatidic acid, and/or mixtures thereof having two fatty acids, such as distearyl-, dipalmitoyl- and/or dioleoyl-phosphatidylcholine, phosphatidylinositol, phosphatidylethanolamine and/or phosphatidic acid, and/or mixtures thereof.

Preferably, the "lecithins and/or derivatives" are derived from natural origins, such as, for example, from egg yolk or soy.

Preferably the ratio of lecithin/essential oil or terpene agent is between 0.3 and 3/1 by weight.

The term emulsifiers refers to ionic and non-ionic emulsifying ingredients, such as non-ionic surfactants that are of the type ethoxylated fatty acid, ethoxylated fatty alcohol, polysorbate 80 etc. . . . These emulsifiers are known per se. According to the present invention, the term "emulsifying agent" refers to any type of agent usually used for this purpose, such as ethoxylated fatty alcohols, ethoxylated fatty acids, ethoxylated alkyl phenols or any other non-ionic product.

The emulsifying agents preferably used in the context of the invention are anionic or nonionic surfactants.

Examples of non ionic surfactants that may be used according to the invention are in particular the condensation product of an aliphatic fatty alcohol, preferably in $C_8$-$C_{22}$, with an alkaline oxide in $C_2$-$C_3$. The alkaline oxide in $C_2$-$C_3$ could be ethylene oxide, propylene oxide or a mixture of ethylene oxide and propylene oxide in any which proportions. An example of such surfactants is the condensation product of lauryl alcohol (or n-dodecyl alcohol) with 30 moles of ethylene oxides.

Non ionic emulsifying agents include sucrose esters, ethoxylated sorbitans monooleate, ethoxylated fatty acids, lecithin, esterified fatty acids such as glycerol oleate and mixtures thereof.

However, the invention is not limited to the use of these specific emulsifying agents.

In the compositions according to the invention, the non ionic emulsifying agents are generally present between 1 and 350 g/L, preferably between 200 and 300 g/L.

In the compositions according to the invention, the anionic emulsifying agents are generally present between 1 and 300 g/L, preferably between 100 and 200 g/L.

In the compositions according to the invention, oils are present between 50 and 350 g/L.

In the compositions according to the invention, terpene agents are present between 20 and 250 g/L.

In the compositions according to the invention, fungicides and/or bactericides are present between 0 and 300 g/L.

A preferred composition according to the invention includes in particular:
 between 0 and 250 g/L of pyrimethanil,
 between 20 and 200 g/L of eugenol,
 between 20 and 200 g/L of lecithin, It may also include other excipients such solubilising agents, for example, organic acid and excipients used to mask the smell of the composition, such as peppermint oil.

The emulsifiable concentrates may be dispersed in water in order to obtain a dilution of the emulsifiable concentrates. According to the invention dilution of the compositions in water may be carried out up to 0.5 to 2%

The compositions in g/L indicated here above and here below are to be understood as being before possible dilution.

Generally, in the method according to the invention, the application of the composition is carried out by means of spraying, dipping or drenching of plants and/or foodstuffs such as fruits and/or vegetables. Preferably the application is carried out by dipping or drenching of fruits and/or vegetables in the emulsifiable concentrate dispersed in water.

According to another embodiment, the compositions according to the invention can be dispersed in the waxes for coating of fruits and/or vegetables.

Application by dipping or drenching is particularly suitable for application carried out post harvesting.

Generally, the composition after dilution is applied in a quantity that enables the application of the fungicidal and/or bactericidal agents in their usual doses, known to the person skilled in the art or at lower doses.

Finally, the invention also relates to the use of an essential oil for the selective treatment of one or more strain(s) of phytopathogenic bacteria and/or fungi resistant to one or more fungicidal and/or bactericidal agent(s).

The embodiments discussed here above and here below are understood to be intended to be considered separately or in each of their combinations.

EXAMPLES

Example 1: Example of a Composition According to the Invention

Emulsifiable Concentrate (in g/L)

| | |
|---|---|
| Non ionic emulsifier | 240 |
| Anionic emulsifier | 180 |
| Essential oils | 160 |
| Pyrimethanil | 190 |
| Lecithin | 60 |
| Mono-propylene glycol | 200 |

Example 2: Fungicidal Activity of the Essential Oils Alone or in Combination with a Synthetic Fungicide, on Resistant or Sensitive Strains The table below shows various fungicidal and/or bactericidal compositions

| | Composition | | |
|---|---|---|---|
| | A | B | C |
| Pyrimethanil | 400 g/L | 192 g/L | — |
| Essential oil/ Terpene agent | — | 140 g/L of eugenol 20 g/L of peppermint oil | 180 g/L of eugenol |
| Lecithin | — | 60 g/L | 250 g/L |
| Total | 1,000 mL | 1,000 mL | 1,000 mL |

Figure 1:
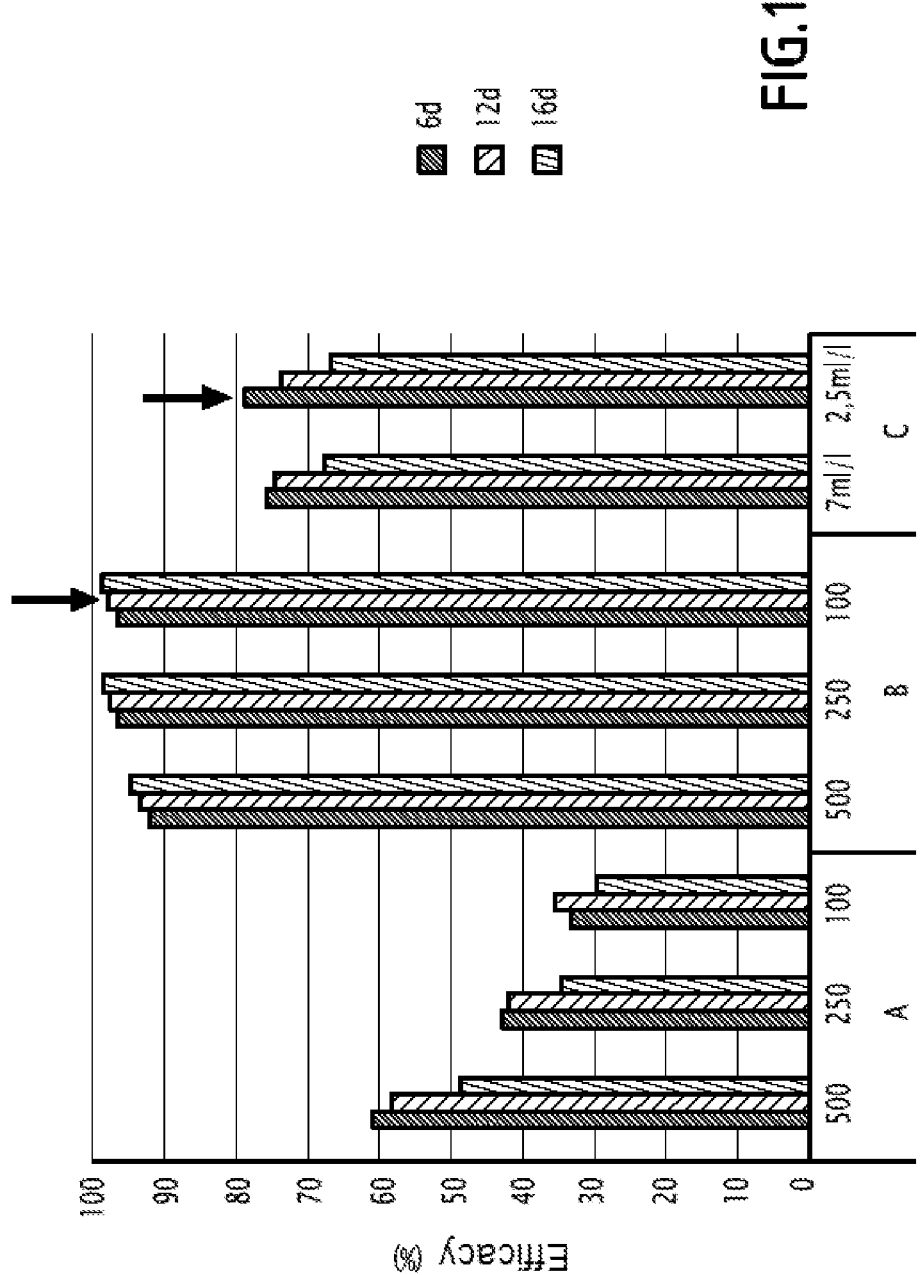
FIG. 1 shows the efficacy of the combinations of the invention on strains of *Penicillium expansum* resistant to pyrimethanil.
Figure 2:
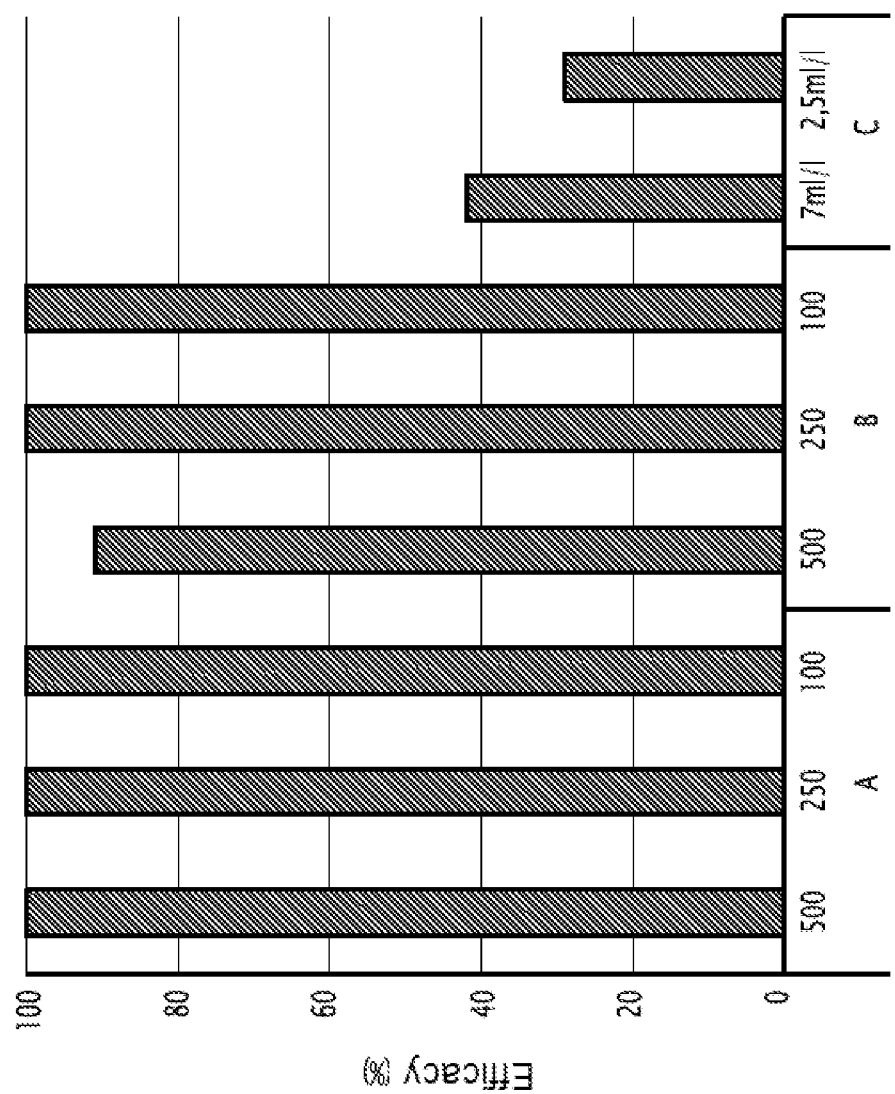
FIG. 2 shows the efficacy of the compositions on the strains of *Penicillium digitatum* that are sensitive to pyrimethanil.

These compositions have been tested on various fungi or bacteria strains, such as illustrated in FIGS. 1 and 2. Unless otherwise indicated, the doses listed in the FIGS. 1 and 2 are given in ppm of active ingredient; the indications in ml/l refer to the quantity of composition C. In FIG. 1 (testing done on "Gala" apples), the composition B, comprising pyrimethanil, eugenol and peppermint oil exhibits an efficacy of between 90 and 100% while pyrimethanil alone at the same dose showed an efficacy of at most 60%. We also see that clove oil alone (composition C) does not exceed 80% efficacy. Indeed it is observed that there is a synergistic effect between the fungicide and essential oils/terpene agents.

In FIG. 2 (tests carried out on lemon), one observes on strains of *Penicillium digitatum* sensitive to pyrimethanil, the efficacy of the composition comprising pyrimethanil and essential oils/terpene agents (composition B). In addition, it is clearly observable that the essential oils/terpene agents alone (composition C) are not effective against susceptible strains, with maximum efficacy at about 40%.

Example 3: Assessment of the In-Vitro Efficacy of Essential Oils Against Phytopathogenic Micro-Organisms Objective of the Study:

The objective of the study was to determine the efficacy of essential oils against phytopathogenic fungi *Penicillium* Spp., *Botrytis* Spp., *Monilinia fructicola* and a bacterium, *Pseudonomas syringae*, compared to commercial synthetic fungicidal and bactericidal products.

The efficacy of samples of essential oils against these phytopathogenic microorganisms was determined by means of counting colonies (determination of CFU colony forming units), cultured at 25° C.+/−1° C. for bacteria and by means of determining the inhibition of the Halo growth for fungi, in accordance with the general guidelines (ISO 6887:2003; ISO 7218:2007; ISO 7954:1987).

Samples Tested:

| Treatment | Active ingredient(s) | Content in active ingredient | Formulation type |
|---|---|---|---|
| Fungazil 500 EC | Imazalil | 50% | EC |
| TECTO SC 500 | Tiabendazole | 42.9% | SC |
| Major C 100 | Alkyl dimethyl benzyl ammonium chloride | 2.5% | SL |
| Xedathane 20 | Pyrimethanil | 20% | EC |
| Bioxeda | Cloves oil | 20% | EC |
| Thymol | Thymol | 18% | EC |
| Carvacrol | Carvacrol | 18% | EC |
| Cinnamon oil | Cinnamaldehyde | 20% | EC |

Description of the Tests Carried Out:

| | Sample | Doses | Application | Duration | Assessment of efficacy |
|---|---|---|---|---|---|
| Phytopathogenic fungus | | | | | |
| *Pennicillum* spp. | 1) Fungazil | Fungazil: 100 ml/hl | By adding into artificial media PDA (Potato Dextrose Agar) | 5 days | Inhibition of growth on Petri dishes |
| | 2) Thymol | Thymol: 100 ml/hl 300 ml/hl 500 ml/hl 1,000 ml/hl | | | |

-continued

| | Sample | Doses | Application | Duration | Assessment of efficacy |
|---|---|---|---|---|---|
| | 3) Fungazil + Thymol | Fungazil + Thymol: 100 ml/hl + 100 ml/hl 100 ml/hl + 300 ml/hl 100 ml/hl + 500 ml/hl 100 ml/hl + 1000 ml/hl | | | |
| *Botrytis* spp. | 1) Tecto SC 500 | Tecto SC 500: 100 ml/hl | By adding into artificial media PDA (Potato Dextrose Agar) | 5 days | Inhibition of growth on Petri dishes |
| | 2) Carvacrol | Carvacrol: 100 ml/hl 300 ml/hl 500 ml/hl 1,000 ml/hl | | | |
| | 3) Tecto SC 500 + Carvacrol | Tecto SC 500 + Carvacrol: 100 ml/hl + 100 ml/hl 100 ml/hl + 300 ml/hl 100 ml/hl + 500 ml/hl 100 ml/hl + 1000 ml/hl | | | |
| *Monilinia fructicola* | 1) Xedathane 20 2) Bioxeda | Xedathane 20: 250 ml/hl Bioxeda: 100 ml/hl 300 ml/hl 500 ml/hl 1,000 ml/hl | By adding into artificial media PDA (Potato Dextrose Agar) | 5 days | Inhibition of growth on Petri dishes |
| | 3) Xedathane 20 + Bioxeda | Xedathane 20 + Bioxeda: 250 ml/hl + 100 ml/hl 250 ml/hl + 300 ml/hl 250 ml/hl + 500 ml/hl 250 ml/hl + 1000 ml/hl | | | |
| Phytopathogenic bacterium | | | | | |
| *Pseudomonas syringae.* | 1) Major C 100 2) Cinnamon oil | Major C 100: 250 ml/hl Cinnamon oil: 100 ml/hl 300 ml/hl 500 ml/hl 1,000 ml/hl | By adding into artificial media NA (nutritional agar) | 24 hours | determination of CFU |
| | 3) Major C 100 + Cinnamon oil | Major C100 + Cinnamon oil 250 ml/hl + 100 ml/hl 250 ml/hl + 300 ml/hl 250 ml/hl + 500 ml/hl 250 ml/hl + 1000 ml/hl | | | |

Description of the Methods:

| Micro-organism | Method | Diluent | Culture media | Replicates | Growth Conditions | Incubation |
|---|---|---|---|---|---|---|
| 1) *Penicillium* spp. 2) *Botrytis* spp. 3) *Monilinia fructicola* 4) *Pseudomonas syringae* | Seeding | Physiological solution | PDA, *Pseudomonas Agar* (only for *P. syringae*) | 4 | 25° C. ± 1° C. | Fungi: 5/6 days Bacteria: 24 h |

Analysis:

The samples were added to the artificial media and gently mixed before solidification of the Agar solution.

Efficacy Against Fungi:

A small amount of fungal spores is placed in the centre of the potato dextrose agar (PDA) in the Petri dishes at 25°±1° C. for 5/6 days. At the end of the incubation period, we measure the inhibition of the halo that is formed in comparison with the untreated PDA Petri dishes (control).

Efficacy Against Bacteria:

A suspension of spores of phytopathogenic microorganisms was prepared and an appropriate amount of dilutions of interest (100 microliters) is added to the petri dishes of *Pseudomonas Agar* and pressed at the agar surface by means of a sterile "L" spatula.

The petri dishes were incubated at 25° C.+1° C. for 24 hours. At the end of the incubation the colony forming units (CFU/ml of product) were determined.

Evaluation of the Results:

The results are indicated as a percentage of the incidence of the disease and the efficacy percentage of the products tested.

*Pennicillum* spp.
Samples:
  Fungazil
  Thymol
  Fungazil+thymol

| Phytopathogenic fungus | Sample | Incidence of Disease (%) | Efficacy (%) | Dose ml/hl |
|---|---|---|---|---|
| *Pennicillum* spp. | Untreated | 100 | 0 | |
| | Fungazil (imazalil) | 5 | 95 | 100 ml/hl |
| | Thymol | 80 | 20 | 100 ml/hl |
| | | 50 | 50 | 300 ml/hl |
| | | 30 | 70 | 500 ml/hl |
| | | 30 | 70 | 1,000 ml/hl |
| | Fungazil + Thymol | 0 | 100 | 100 + 100 ml/hl |
| | | 0 | 100 | 100 + 300 ml/hl |
| | | 0 | 100 | 100 + 500 ml/hl |
| | | 0 | 100 | 100 + 1,000 ml/hl |

*Pennicillum* spp.—Strain Resistant to Imazalil
Samples:
  Fungazil
  Thymol
  Fungazil+thymol

| Phytopathogenic fungus | Sample | Incidence of Disease (%) | Efficacy (%) | Dose ml/hl |
|---|---|---|---|---|
| *Pennicillum* spp. Strain resistant to Imazalil | Untreated | 100 | 0 | |
| | Fungazil | 85 | 15 | 100 ml/hl |
| | Thymol | 30 | 70 | 100 ml/hl |
| | | 30 | 70 | 300 ml/hl |
| | | 20 | 80 | 500 ml/hl |
| | | 10 | 90 | 1,000 ml/hl |
| | Fungazil + Thymol | 10 | 90 | 100 + 100 ml/hl |
| | | 10 | 90 | 100 + 300 ml/hl |
| | | 5 | 95 | 100 + 500 ml/hl |
| | | 0 | 100 | 100 + 1,000 ml/hl |

*Botrytis* spp.—Strain Resistant to Thiabendazole
Samples:
  Tecto SC 500
  Carvacrol
  Tecto SC 500+Carvacrol

| Phytopathogenic fungus | Sample | Incidence of Disease (%) | Efficacy (%) | Dose ml/hl |
|---|---|---|---|---|
| *Botrytis* spp. Strain resistant to TBZ | Untreated | 100 | 0 | |
| | TBZ | 100 | 0 | 100 ml/hl |
| | Carvacrol | 0 | 100 | 100 ml/hl |
| | | 0 | 100 | 300 ml/hl |
| | | 0 | 100 | 500 ml/hl |
| | | 0 | 100 | 1,000 ml/hl |
| | TBZ + Carvacrol | 0 | 100 | 100 + 100 ml/hl |
| | | 0 | 100 | 100 + 300 ml/hl |
| | | 0 | 100 | 100 + 500 ml/hl |
| | | 0 | 100 | 100 + 1,000 ml/hl |

*Monilinia fructicola*
Samples:
  Xedathane 20
  Bioxeda
  Xedathane 20+Bioxeda

| Phytopathogenic fungus | Sample | Incidence of Disease (%) | Efficacy (%) | Dose ml/hl |
|---|---|---|---|---|
| *Monilinia fructicola* | Untreated | 100 | 0 | |
| | Xedathane 20 | 5 | 95 | 250 ml/hl |
| | Bioxeda | 75 | 25 | 100 ml/hl |
| | | 70 | 30 | 300 ml/hl |
| | | 30 | 70 | 500 ml/hl |
| | | 20 | 80 | 1,000 ml/hl |
| | Xedathane 20 + Bioxeda | 0 | 100 | 250 + 100 ml/hl |
| | | 0 | 100 | 250 + 300 ml/hl |
| | | 0 | 100 | 250 + 500 ml/hl |
| | | 0 | 100 | 250 + 1000 ml/hl |

*Monilinia fructicola*—Strain Resistant to Pyrimethanil
Samples:
    Xedathane 20
    Bioxeda
    Xedathane 20+Bioxeda

| Phytopathogenic fungus | Sample | Incidence of Disease (%) | Efficacy (%) | Dose ml/hl |
|---|---|---|---|---|
| *Monilinia fructicola* Strain resistant to Pyrimethanil | Untreated | 100 | 0 | |
| | Xedathane 20 | 55 | 45 | 250 ml/hl |
| | Bioxeda | 30 | 70 | 100 ml/hl |
| | | 20 | 80 | 300 ml/hl |
| | | 25 | 75 | 500 ml/hl |
| | | 20 | 80 | 1,000 ml/hl |
| | Xedathane 20 + Bioxeda | 10 | 90 | 250 + 100 ml/hl |
| | | 5 | 95 | 250 + 300 ml/hl |
| | | 3 | 97 | 250 + 500 ml/hl |
| | | 5 | 95 | 250 + 1000 ml/hl |

*Pseudomonas syringae*—Strain Resistant to Quaternary Ammonium Compounds
Samples:
    Major C 100
    Cinnamon oil
    Major C 100+Cinnamon oil

| Phytopathogenic fungus | Sample | Incidence of Disease (%) | Efficacy (%) | Dose ml/hl |
|---|---|---|---|---|
| *Pseudomonas syringae* Strain resistant to quaternary ammonium compounds | Untreated | 100 | 0 | |
| | Major C 100 | 75 | 25 | 250 ml/hl |
| | Cinnamon oil | 70 | 30 | 100 ml/hl |
| | | 35 | 65 | 300 ml/hl |
| | | 5 | 95 | 500 ml/hl |
| | | 5 | 95 | 1,000 ml/hl |
| | Major + Cinnamon oil | 35 | 65 | 100 + 100 ml/hl |
| | | 25 | 75 | 100 + 300 ml/hl |
| | | 0 | 100 | 100 + 500 ml/hl |
| | | 0 | 100 | 100 + 1,000 ml/hl |

CONCLUSION

The plant essential oils show a broad spectrum of activity against fungi, phytopathogenic bacteria, which may be summarised as follows:

*Penicillium* spp.:
The fungi are present in 100% of the untreated Petri dishes. Thymol shows moderate activity (efficacy comprised between 20% and 70% at a dose of between 100 and 1,000 ml/hl), whereas the combination of thymol and Imazalil enables full control at all the doses tested.

*Penicillium* spp., Strain Resistant to Imazalil.
The fungi are present in 100% of the untreated Petri dishes. The thymol shows strong activity (efficacy comprised between 70 and 90% at a dose of between 100 and 1,000 ml/hl). Total control may be achieved by the combination of Imazalil and thymol at the dose of 100+1,000 ml/hl.

*Botrytis* spp., Strain Resistant to Thiabendazole.
The fungi are present in 100% of the untreated Petri dishes.
Thiabendazole shows no efficacy at a dose of 100 ml/hl, while carvacrol allows total control of this strain at all doses tested. The same holds true for the combination of thiabendazole and carvacrol.

*Monilinia fructicola*:
The fungi are present in 100% of the untreated Petri dishes.
Clove oil enables moderate control of fungi at all doses tested, while clove oil in combination with pyrimethanil allows total control of fungi at all doses tested.

*Monilinia fructicola*, Strain Resistant to Pyrimethanil:
Pyrimethanil enables only 45% efficacy, while the clove oil allows efficacy of between 70 and 80% at all doses tested.
The combination of clove oil and pyrimethanil allows almost total control at the doses tested.

*Pseudomonas syringae*, Strain Resistant to Quaternary Ammonium Compounds.
The bacterium is present in 100% of the untreated Petri dishes.
The quaternary ammonium tested shows an efficacy of only 25% whereas the cinnamon oil enables an efficacy of up to 80% at 1,000 ml/hl.
The combination of quaternary ammonium with cinnamon oil allows full control at all doses of cinnamon oil tested and at a dose that is less than half the comparison dose of the quaternary ammonium compound (100 ml/hl vs. 250 ml/hl).

The invention claimed is:

1. A method for fungicidal and/or bactericidal treatment of one or more phytopathogenic strain(s) of fungi and/or bacteria resistant to one or more synthetic fungicidal and/or bactericidal agent(s) comprising:
    applying a composition comprising clove oil on plants or foodstuffs that are infected by said phytopathogenic strain; and
    applying one or more said synthetic fungicidal and/or bactericidal agent(s) on said plants or said foodstuffs,
    wherein the clove oil and the fungicidal and/or bactericidal agent(s) are applied in a ratio of the clove oil to the fungicidal and/or bactericidal agent(s) part of between 0.3 and 3,
    wherein said one or more said synthetic fungicidal and/or bactericidal agent(s) is pyrimethanil, and
    wherein said phytopathogenic strain is *Penicillium digitatum*.

2. The method according to claim 1, wherein the fungicidal and/or bactericidal agent(s) is (are) applied simultaneously with the clove oil, or separately.

3. The method according to claim 1, wherein the application is carried out before or after harvesting.

4. The method according to claim 1, wherein the application of the said composition is carried out by means of spraying, dipping and/or drenching.

5. The method according to claim 1, wherein the composition further comprises one or more emulsifiers.

6. The method according to claim 1, wherein said composition before dilution comprises between 50 and 350 g/L with respect to clove oil, before eventual dilution.

7. The method according to claim 5, wherein the composition is in the form of an emulsifiable concentrate and that the method further comprises a preliminary step of dispersing said concentrate in water before application.

8. The method according to claim 1, wherein said composition comprising clove oil and said one or more fungicidal and/or bactericidal agent(s) are both applied, simultaneously or separately, before harvesting said plants or said foodstuffs.

9. The method according to claim 1, wherein said clove oil in combination with said one or more synthetic fungicidal and/or bactericidal agent(s) has a synergistic effect.

\* \* \* \* \*